(12) United States Patent
Karnes et al.

(10) Patent No.: US 11,786,266 B2
(45) Date of Patent: Oct. 17, 2023

(54) VARIABLE PARTICLE SIZE TISSUE COLLECTOR

(71) Applicant: ARTHREX, INC., Naples, FL (US)

(72) Inventors: G. Joshua Karnes, Estereo, FL (US); Shane Noble, Naples, FL (US); Christopher Bare, Naples, FL (US); Andrea Matuska, Naples, FL (US)

(73) Assignee: Arthrex, Inc., Naples, FL (US)

( * ) Notice: Subject to any disclaimer, the term of this patent is extended or adjusted under 35 U.S.C. 154(b) by 167 days.

(21) Appl. No.: 17/174,457

(22) Filed: Feb. 12, 2021

(65) Prior Publication Data

US 2021/0251647 A1   Aug. 19, 2021

Related U.S. Application Data (60) Provisional application No. 62/976,639, filed on Feb. 14, 2020.

(51) Int. Cl.
*A61B 17/32* (2006.01)
*A61B 17/22* (2006.01)

(52) U.S. Cl.
CPC ...... *A61B 17/320016* (2013.01); *A61B 17/22* (2013.01); *A61B 2017/22079* (2013.01); *A61B 2217/005* (2013.01)

(58) Field of Classification Search
CPC ............ A61B 17/320016; A61B 17/22; A61B 2017/22079; A61B 2217/005; A61M 2205/7545; A61M 1/79
See application file for complete search history.

(56) References Cited

U.S. PATENT DOCUMENTS

| | | | |
|---|---|---|---|
| 7,008,394 B2 * | 3/2006 | Geise | A61M 1/0236 604/6.15 |
| 8,632,562 B2 * | 1/2014 | Pal | A61F 2/012 606/200 |
| 8,967,513 B1 | 3/2015 | Rouzbeh et al. | |
| 9,555,169 B2 * | 1/2017 | Segina | A61L 27/3608 |
| 9,909,103 B2 * | 3/2018 | Howard | A61B 17/32002 |
| 10,342,552 B2 | 7/2019 | Assell et al. | |
| 2006/0037903 A1 * | 2/2006 | Smith | G01N 1/40 210/240 |
| 2018/0344327 A1 | 12/2018 | Jeng | |
| 2019/0262031 A1 | 8/2019 | Efremkin | |

FOREIGN PATENT DOCUMENTS

WO    2014163954 A1    10/2014

* cited by examiner

*Primary Examiner* — Ariana Zimbouski
*Assistant Examiner* — Katherine-Ph Minh Pham
(74) *Attorney, Agent, or Firm* — Lathrop GPM LLP; Lisa Hillman (57) ABSTRACT

Devices and methods for collecting tissue fragments of variable sizes from a surgical site are described herein. The devices can include at least two filters having a different pore size for the collection and sorting of tissue fragments by size.

25 Claims, 3 Drawing Sheets

VARIABLE PARTICLE SIZE TISSUE COLLECTOR

CROSS REFERENCE TO RELATED APPLICATIONS

This application claims the benefit under 35 USC § 119(e) to U.S. Application Ser. No. 62/976,639 filed Feb. 14, 2020. The disclosure of this application is considered part of and is incorporated by reference hereby in the disclosure of this application.

BACKGROUND

Various devices can be used for resecting and collecting tissue fragments. There is a need, however, for devices and methods for resecting and collecting tissue fragments while simultaneously differentiating tissue fragment by size.

SUMMARY OF THE DISCLOSURE

Devices for the resection of tissue fragments can generate particles with varying size, and the size range of resected particles can vary from one resecting device to another. The size of the particles used in grafts of tissue fragments can affect the long-term performance of a graft in vivo. Therefore, there is a need for improved devices and methods for collecting tissue fragments and differentiating the fragments based on particle size. Such devices and methods will have substantial application in orthopedics, for example.

An embodiment provides a device for collecting tissue fragments of variable sizes from a surgical site. Devices can include:
  a top housing comprising a first universal adapter,
  at least two filters each having a different pore size,
  a filter distractor, and
  a bottom housing comprising a second universal adapter,
    wherein the at least two filters are assembled in series onto the filter distractor; wherein the filter distractor and the at least two filters are inserted into the top housing or bottom housing; and wherein the top housing and the bottom housing are assembled together into a container.

Another embodiment provides a method of collecting tissue fragments of separate, variable sizes. Methods can include:
  providing a device including a top housing comprising a first universal adapter, at least two filters each having a different pore size, a filter distractor, and a bottom housing comprising a second universal adapter, wherein the at least two filters are assembled in series onto the filter distractor; wherein the filter distractor and the at least two filters are inserted into the bottom housing; and wherein the top housing and the bottom housing are assembled together into a container;
  connecting the first universal adapter of the device to a second device for resecting tissue fragments, collecting tissue fragments, or resecting and collecting tissue fragments;
  connecting the second universal adapter of the device to a suction or aspiration apparatus; and
  collecting tissue fragments on the at least two filters.

An additional embodiment provides an assembly for collecting tissue fragments of variable sizes from a surgical site comprising two or more devices each including a top housing comprising a first universal adapter, at least two filters each having a different pore size, a filter distractor, and a bottom housing comprising a second universal adapter, wherein the at least two filters are assembled in series onto the filter distractor; wherein the filter distractor and the at least two filters are inserted into the top housing or bottom housing; and wherein the top housing and the bottom housing are assembled together into a container. The two or more devices can each be connected to a device for resecting tissue fragments from a surgical site though each of the first universal adapters. The two or more devices can each be connected to a suction or aspiration device through the each of the second universal adaptors. The two or more devices can be connected through the first universal adapters to a valve that can control the flow of fluid to the two or more devices.

Yet another embodiment provides a method of collecting tissue fragments of separate, variable sizes. Methods can include providing an assembly for collecting tissue fragments of variable sizes from a surgical site comprising two or more devices as described herein. The first universal adaptor of each device can be connected to a device for resecting tissue fragments. The second universal adapter of each device can be connected to an aspiration or suction device. A valve can be present between the first universal adapters and the device for resecting tissue fragments. Tissue fragments can be collected on the at least two filters of the two or more devices.

BRIEF DESCRIPTION OF THE DRAWINGS

The accompanying drawings are included to provide a further understanding of the methods and compositions of the disclosure, are incorporated in, and constitute a part of this specification. The drawings illustrate one or more embodiments of the disclosure, and together with the description serve to explain the concepts and operation of the disclosure.

DETAILED DESCRIPTION

Problem to be Solved

Devices for the resection of tissue fragments can generate particles having varying sizes, depending on the tissue and on the type of resecting device. For example, an arthroscopic shaver assembled with different blades can generate particles of various size ranges. Tissue fragments collected in this manner can be used in grafts; however, the long-term performance of the graft in vivo can be affected by the size of the particles used in the graft. There is an unmet need for devices and methods for collecting tissue fragments and sorting the fragments by size. The present devices and methods are provided to address this unmet need.

Variable Particle Size Collector Device

A device for collecting tissue fragments of variable sizes from a surgical site can comprise, for example, a top housing including a first universal adapter, at least two filters each having a different pore size, a filter distractor, and a bottom housing including a second universal adapter for the collection of variable particle sizes of tissue. At least two filters can be assembled in series onto the filter distractor such that the filter distractor and the at least two filters can be inserted into the top housing or bottom housing. The top housing and the bottom housing can be assembled together to form a container. A device can be configured such that a fluid can enter the device by the first universal adapter, flow from the top housing to the bottom housing through the filters and exit the device by the second universal adapter.

A device can include at least two filters each having a different pore size, which can be assembled in series so that a fluid can flow from a filter having a larger pore size to a filter having a smaller pore size. The filter can be a cup-shaped filter having a bottom and one or more side walls. A filter can be configured such that the bottom fully or partially comprises filter material (e.g. mesh), the one or more side walls fully or partially comprises filter material, or the bottom and the side walls fully or partially comprise filter material.

A filter distractor can be configured so that it can fit through the middle of the bottom of each cup-shaped filter and so that it can be configured to remove tissue from the filters. The top and the bottom housing can both include a connector such as screw thread. For example, the top housing can include an internal screw thread and the bottom housing can include an external screw thread, or the top housing can include an external screw thread and the bottom housing can include an internal screw thread. The internal screw thread and external screw thread can be designed to be complementary to one another so that the top housing and the bottom housing fit together to form a sealed, sterile container. Alternatively, the top housing and the bottom housing can be assembled together using a press-fit mechanism. Any suitable connector for the top and bottom housing can be used.

A first universal adapter can be configured so that a second device for resecting or collecting tissue fragments from a surgical site, such as an endoscopic shaver, an endoscopic bone cutter, an endoscopic burr, an endoscopic drill, or a suction wand can be connected to the device. A second universal adapter can be configured to that a suction or aspiration apparatus can be connected to the device.

The at least two filters can be present as a modular assembly such that one or more filters can be removed or added to the filter distractor A bottom housing can be designed to include a clear material. Graduated marks for measuring a volume of tissue fragments collected in each filter can be included on a housing.

Methods are provided herein for collecting tissue fragments of separate, variable sizes. In some aspects, a device including a top housing including a first universal adapter, at least two filters each having a different pore size, a filter distractor, and a bottom housing including a second universal adapter is provided, such that the first universal adapter of the device can be connected to a second device for resecting tissue fragments, collecting tissue fragments, or resecting and collecting tissue fragments; the second universal adapter can be connected to a suction or aspiration apparatus; and tissue fragments can be collected on the at least two filters. In some aspects, the tissue is soft tissue, bone or cartilage. In other aspects, the second device for resecting tissue fragments is an arthroscopic shaver, an arthroscopic bone cutter, an arthroscopic burr, or an arthroscopic drill.

In one aspect, the device comprises three filters. For example, a first filter has about 750 micron to about 850 micron pores, so that tissue fragments having a size equal or greater than about 750 microns to about 850 microns can be collected; a second filter has about 350 micron to about 450 micron pores, so that tissue fragments having a size ranging from about 350 microns to about 850 microns can be collected; and a third filter has about 50 micron to about 100 micron pores, so that tissue fragments having a size ranging from about 50 microns to about 450 microns can be collected. The tissue fragments can be contained within a fluid, which can flow through the filters. Additionally, the method can includes removing the top housing to access the filter distractor and the filters containing the tissue fragments of variable sizes. The filters can be pulled out of the bottom housing using the filter distractor. The filters can be configured so that the filters can be removed from the filter distractor individually.

Figure 1:
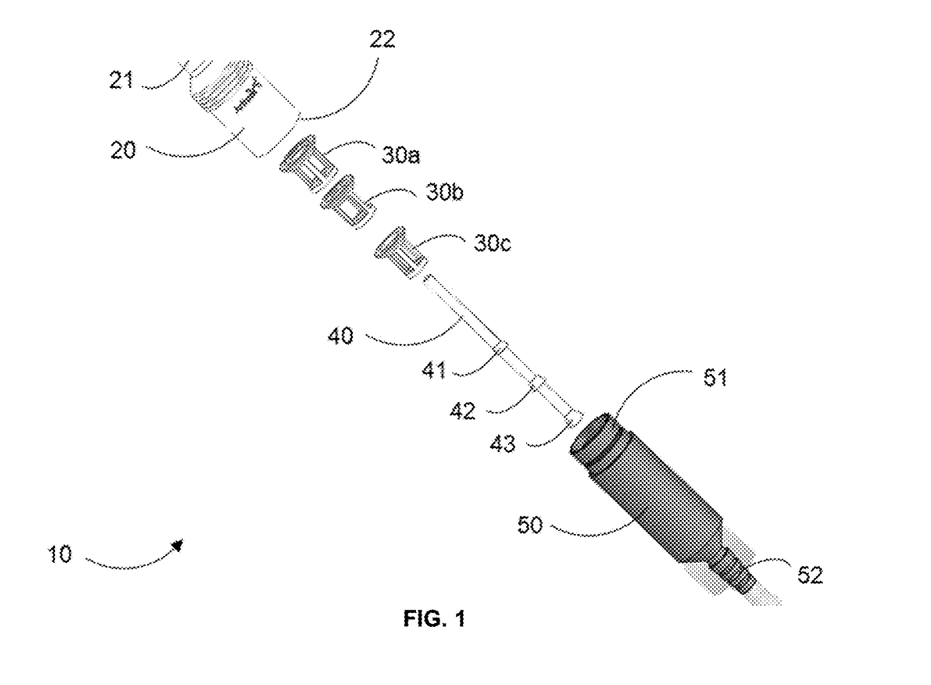
FIG. 1 illustrates a perspective view of a disassembled device comprising three filters.

Aspects of a variable particle size tissue collector are exemplified herein at inter alia, FIGS. 1-4. Referring to FIG. 1, illustrating a disassembled device (10) in a perspective view, a top housing (20), filters (30*a*, 30*b*, and 30*c*), a filter distractor (40), and a bottom housing (50) are individually represented.

Housings

A top housing (20) can include a generally tubular body, or any other suitable shape, with an aperture running from a first terminus, where it can include a first universal adapter (21), to the second terminus, where it can include a screw thread, or a press-fit (22), or other connector. A bottom housing (50) can include a generally tubular body, or any other suitable shape, with an aperture running from a second terminus, where it can include a screw thread, or a press-fit (51), or any other suitable connector, to the first terminus, where it can include a second universal adapter (52). An aperture running lengthwise of the bottom housing can accommodate the filters assembled onto the filter distractor. The housings can have one terminus that is narrower than the other, for example the narrower terminus can include a universal adapter, and the wider terminus can comprise screw threads, press-fit, or another suitable connector. Alternatively, an aperture running lengthwise of the top housing can accommodate the filters assembled on the filter distractor in the same way as the bottom housing.

Figure 2:
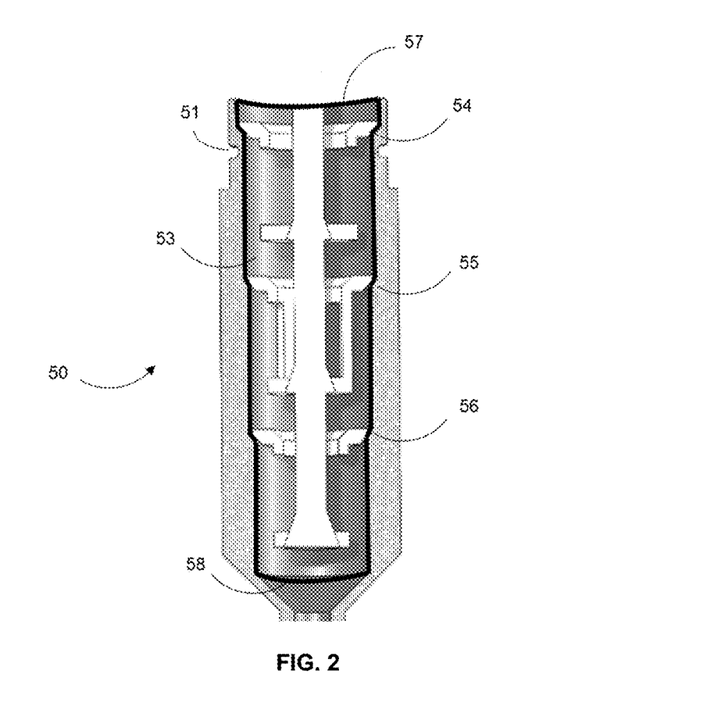
FIG. 2 illustrates a cross-section view of a bottom housing, detailing the bottom housing interior shape.

In one embodiment shown in FIG. 2, the bottom housing aperture, running lengthwise does not have a linear shape. The generally tubular or cylindrical aperture (53) can be tapered or can include, for example, ridges (54, 55, and 56), such that the diameter of the aperture gradually reduces, from its largest at the wider terminus (57), to its smallest at the narrower terminus (58). The ridges can provide additional support to the filters, which are assembled onto the filter distractor.

The top housing and the bottom housings can be made of polypropylene or another any other suitable solid, nonabsorbent material, and can be partially or fully translucent for visibility. The bottom housing can be designed to further include graduated marks for measuring a volume of tissue fragments collected in each filter.

The top and the bottom housing can both include screw threads, press-fit, or another suitable connector (see FIG. 1). For example, the top housing can include an internal screw thread (22) and the bottom housing can include an external screw thread (51), or alternatively, the top housing can include an external screw thread and the bottom housing can include an internal screw thread. The internal screw thread and external screw thread are designed to be complementary to one another, so that the top housing and the bottom housing fit together to form a sealed, sterile container. Alternatively, a top and a bottom housing can both include a press-fit mechanism. A press-fit mechanism can be used to fasten the top housing to the bottom housing. A press-fit mechanism, interference fit, or friction fit is a fastening between two parts (i.e., the top housing and the bottom housing), which can be achieved by friction after the parts are pushed together, rather than by any other means of fastening, such as a screw thread for example. The pressing operation can lead to a mechanical joint between the top housing and the bottom housing, leading the assembly of the sterile container. Pressing operation leads to a mechanical joint between the tube and the fitting.

Filters

A device can include at least two filters (30) (e.g., 2, 3, 4, 5, 6, 7, or more), assembled in series onto a filter distractor. The filter can be a cup-shaped filter, as exemplified in FIG. 3, having a bottom (33), and one or more side walls. The cup-shaped filter can have a round or ovoid bottom. In this case, one continuous side wall is present. See e.g., FIG. 3. However, other shapes are possible for the bottom, including for example, a square, rectangle, or hexagon. In this case, there will be several side walls (e.g., 4 side walls in the case of a square bottom). The bottom of the filter can comprise a filter material between an aperture (35) for a filter distractor and a point where the bottom meets the sidewall. The bottom of the filter can comprise a solid material between an aperture (35) for a filter distractor and a point where the bottom meets the sidewall. The one or more sidewalls can comprise a filter material, a solid material, or a combination of a filter material and a solid material. Both the bottom of the filter (33) and the one or more side walls can comprise filter material. The cup-shaped filter can include a first solid ring (31) (or other appropriate shape) at the top of the filter for support. The cup-shaped filter can comprise any appropriate support for the one more side walls. For example, one or more solid legs (e.g., 1, 2, 3, 4, or more) (32) can be present along the one or more side walls. For additional support, a cup-shaped filter can comprise a solid ring (or other appropriate shape) circumscribing the bottom (34). The bottom solid ring can provide support for the bottom filter material (33), which can include an aperture in the center (35) for assembly onto the filter distractor.

Figure 3:
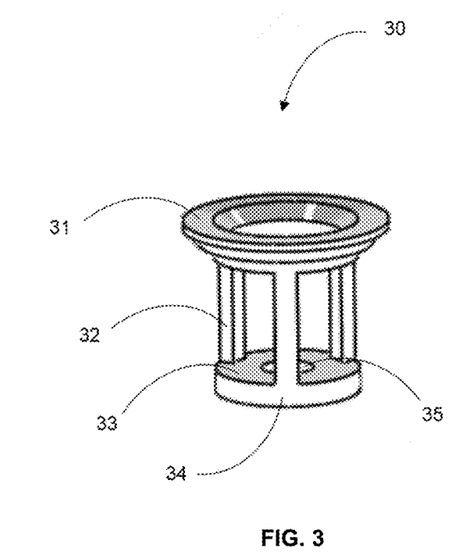
FIG. 3 illustrates a perspective view of a cup-shaped filter.

A first solid ring (or other appropriate shape) at the top of a filter (31) can rest on one or more ridges (54, 55, or 56) inside the bottom housing. The number of ridges can correspond to the number of filters in the device. In an exemplary aspect, the filter top and bottom are circular, and supported by solid rings to accommodate into a generally tubular housing, for example, the bottom housing; however, those shapes can vary with the shape of the device. The side walls can fully include filter material, from the top ring to the bottom ring, can partially include filter material and partially include solid material, or can be partially solid and partially open.

The solid parts of the filter (e.g., top ring, bottom ring, and legs) can comprise polystyrene or another solid, nonabsorbent material, and can be partially or fully translucent for visibility. The filter material can include a membrane or a mesh having pores, which can have varying size. The filter material can comprise for example, metals or plastics, like titanium, stainless steel, polyethylene, polytetrafluoroethylene PTFE, polyvinylidene fluoride (PVDF), nylon, polypropylene (PP), polyester, polycarbonate, polyethersulfone, cellulose acetate, polyimide, or another equivalent material. A filter can have a pore size ranging from about 50 microns to about 1000 microns. For example, a filter can have about 50 micron to about 100 micron pores, about 100 micron to about 200 micron pores, about 200 micron to about 300 micron pores, about 300 micron to about 400 micron pores, about 400 micron to about 500 micron pores, about 600 micron to about 600 micron pores, about 600 micron to about 700 micron pores, about 700 micron to about 800 micron pores, about 800 micron to about 900 micron pores, or about 900 micron to about 1000 micron pores. In an exemplary device, including three filters, the first filter can have about 750 micron to about 850 micron pores, so that tissue fragments having a size equal or greater than about 750 microns to about 850 microns can be collected; the second filter can have about 350 micron to about 450 micron pores, so that tissue fragments having a size ranging from about 350 microns to about 850 microns can be collected; and the third filter can have about 50 micron to about 100 micron pores, so that tissue fragments having a size ranging from about 50 microns to about 450 microns can be collected.

The device can include at least two filters (e.g., 2, 3, 4, 5, 6, 7, or more) having a different pore sizes, assembled in series so that the fluid can flow from a filter having a larger pore size to a filter having a smaller pore size. For example, in the device described in FIG. 4, three filters, 30*a*, 30*b*, and 30*c*, are assembled onto the filter distractor; as the fluid flows from the top housing to the bottom housing, the fluid flows first into filter 30*a*, then into filter 30*b*, and lastly into filter 30*c* before exiting the device. In such an example, filter 30*a* would have a larger size pore than filter 30*b*, and filter 30*b* would have a larger pore size than filter 30*c*.

The filters can be present as a modular assembly. As used herein, a "modular assembly" refers to the adaptability of the assembly of a device such that filters can individually be added or removed depending upon the needs of a user. For example, if a device is configured so that it can comprise 5 filters, some filters can be removed while some others are assembled in the device, without altering the functionality or method of use of the device. For example, 2 or 3 out of the 5 filters can be added and used and the others can be removed in order to accommodate for collection of a particular particulate size. Furthermore, if a user wanted to add additional filters, the extra filters can be easily added to the filter distractor.

Filter Distractor

The device includes a filter distractor for the in-series assembly of the filters. As exemplified in FIG. 4, a filter distractor (40) can be configured so that it can fit through the middle of the bottom of the cup-shaped filters, and so that the filters assembled onto the filter distractor can be accommodated into the aperture of, e.g., the top or bottom housing (53). The filter distractor can optionally be configured to that it can be used to remove tissue from the filters.

Figure 4:
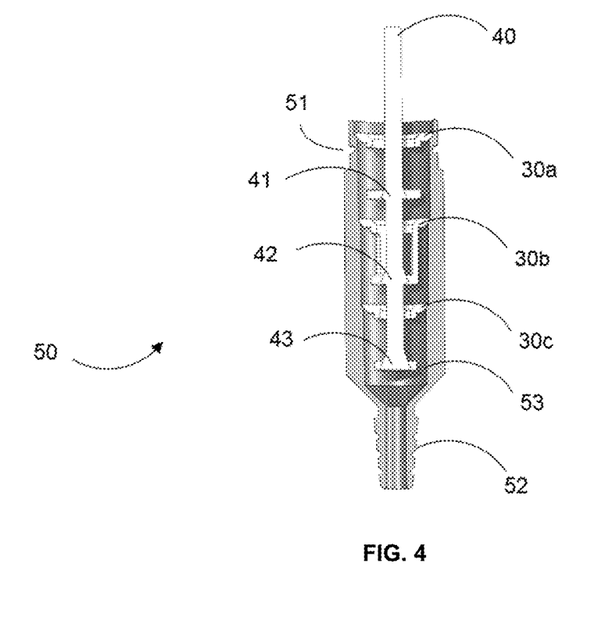
FIG. 4 illustrates a cross section view of a bottom housing, showing how the filters are assembled onto the filter distractor, and how filter distractor and filters fit into the bottom housing.

The filter distractor can comprise a rod having a length that is greater than the length of the, e.g., bottom housing, so that a portion of the rod stands out or sticks out of the bottom housing, but is short enough so that the entire rod can fit into the assembled device (i.e., top and bottom housing assembled into a container, with the filter distractor and the filters contained within). The rod can include at least two ridges, at least three ridges (41, 42, and 43), or at least 4, 5, 6, 7, or more ridges to hold the at least two filters in place, and includes as many ridges as the device has filters. The ridges are designed so that the ridge that is the closest to the narrow terminus of the bottom housing is the widest, and the ridge that is the closest to the wide terminus of the bottom housing is the smallest. The size of the ridge on the filter distractor can be configured so that a filter can be accommodated onto the ridge through its aperture (35) located in the center of the bottom surface of the filter (33) (see FIG. 3). As exemplified in FIG. 4, which illustrates a device with three filters (filter 30a, filter 30b and filter 30c), wherein each filter rests on a ridge of the filter distractor having a different size (see 41, 42, and 43). To be able to fit on the ridge, each filter has an aperture (35) having a size adapted to the size of the ridge it is resting onto. For example, in a device as illustrated in FIG. 4, filter 30a, which would have the largest pore size, would rest onto the smallest of the ridge (41) of the filter distractor (40). To accommodate the size of the ridge, filter 30a would have the smallest aperture (35) on the bottom surface. Filter 30c, which would have the smallest pore size, would rest onto the largest ridge (43) of the filter distractor. To accommodate to size of the ridge, filter 30c would have the largest aperture (35) on the bottom surface. Filter 30b, located between filter 30a and filter 30c, which would have an intermediate pore size (e.g., a pore size larger than the smallest pore size, but smaller than the largest pore size), would rest on a ridge having an intermediate size (42) (e.g., a ridge larger than the smallest ridge, but smaller than the largest ridge) on the filter distractor. To accommodate to the size of the ridge, filter 30b would have an aperture of intermediate size on the bottom surface When the device is configured such that a bottom housing can accommodate a filter distractor and two or more filters, during use, the suction applied by the aspiration device at the terminus of the bottom housing (where it includes an universal adapter) can aid the stability of the filters onto the filter distractor (e.g., onto the ridges of the filter distractors, 41, 42, 43) and onto the ridges inside the bottom housing (54, 55, 56). That is, by pressing the filter down into the bottom housing, the suction can help stabilize the filters inside the bottom housing by further pressing the filters on the ridges (e.g., onto the filter distractor and inside the bottom housing).

When the device is configured such that a top housing can accommodate a filter distractor and two or more filters, during use, the suction applied by the aspiration device at the terminus of the bottom housing (where it includes an universal adapter) can aid the stability of the filters onto the filter distractor (e.g., onto the ridges of the filter distractors, 41, 42, 43). To further stabilize the filters inside a top housing, a hook, locking, or twisting mechanism can be incorporated into the filters to temporarily fix or attach the filters to the filter distractor. The two or more filters can be stably attached to the filter distractor prior to the tissue fragment collection process (e.g., using a screw thread, press-fit, or another suitable connector), such that the filter can remain stable inside the top housing during the tissue collection process, and then be easily detached from the filter distractor once the collection process is completed.

Furthermore, the filter distractor can be configured to aid in the removal of tissue from the filter. The distractor can be configured to form a floor or disc at the bottom of each filter. A floor or disc can be made of a solid material (e.g., the same material as the filter distractor), or made of filter material. A floor or disc can be configured to partially or fully cover the bottom of the filter (33). In the case of a cup-shapes filter, with the bottom of the filter having a circular shape, a floor or disc can have a circular shape, that covers part of all of the surface of the bottom of the filter. For example, the floor or disc can be slightly smaller than surface of the bottom of the filter (e.g., the floor or disc can have an inner diameter slightly smaller than an inner diameter of the bottom of the filter, such that the floor or disc fits easily inside the filter, and covers its entire surface. After a filter has collected tissue fragments a user can pull the distractor up such that the floor or disc comes up and out of each filter. Tissue fragments collected on the disc or floor and can be removed and disposed into to a collection container. The shape of the floor can be configured to be suitable for the shape of the filter. That is, a device configured to host cube-shapes filters, with a square bottom, can comprise a filter distractor including a floor at a ridge, where the floor has a square shape.

Alternatively, a filter distractor can be configured to include a scoop or fin feature that can make contact with a part of each filter wall. The scoop or fin is attached to the distractor rod, for example where the rod comprises a ridge, such that a scoop or fin can contact the bottom (and optionally also the side walls) of a filter, to scrap tissue fragments from the filter, and ease their collection from the filter. When tissue fragments are collected in a filter, a user can rotate the filter distractor within the filter and the scoop or fin feature will collect or free the tissue from the filter. The tissue can then be moved to a collection container.

A filter distractor can comprise both a floor or disc (e.g., to ease the removal of the tissue fragments from the filter) and a scoop or fin (e.g., to scrap and detach the tissue fragments from the side walls and from the bottom of the filter, or from the floor or disc).

The filter distractor can be made of polypropylene or another solid, nonabsorbent material.

The filters can be installed on the filter distractor individually, by starting with the filter that would seat on a larger ridge and finishing with the filter that would seat on a smaller ridge. The filter distractor, assembled with the filters, can be introduced into the bottom housing, where the ridges can define the appropriate position of the filters. Alternatively, the filter distractor, assembled with the filters can be introduced into the top housing. The rod length can vary and is defined by the length of the assembled device (e.g., including both the top and the bottom housings), which can fluctuate depending on the number of filters. The rod length is defined so that it accommodates all the filters of the device, and so that a portion of the rod can stand out or stick out of the bottom housing (or top housing) to be grabbed by a user for removal.

Adapters

The device can include a first universal adapter (21), as part of the top housing, and a second universal adapter (52), as part of the bottom housing. The first universal adapter can be configured so that a second device for resecting or collecting tissue fragments from a surgical site, such as an endoscopic shaver, an endoscopic bone cutter, an endoscopic burr, an endoscopic drill, a suction wand, or the like can be connected to the device. The second universal adapter can be configured so that a suction or aspiration apparatus can be connected to the device. As used herein, the term "universal adaptor" refers to any universal hose or fitting, regardless of its shape. The device can include a first and a second adapter that are universal adapters, so that virtually any resecting or collecting device can be connected to the first adapter, and virtually any suction or aspiration device can be connected to the second adapter, regardless or the brand, connection, and characteristics of said devices. A first universal adapter and a second universal adapter are provided for the easy assembly of the device. Any suitable adaptor can be used.

Methods of Use

Methods for collecting tissue fragments of separate, variable sizes are provided. A device, as described above, can be provided fully assembled. Such fully assembled device can be provided as a sterile device, ready to use in a clinical or other sterile environment for tissue fragment collection. A method can include the assembly of the device with a second device for resecting tissue fragments, collecting tissue fragments, or resecting and collecting tissue fragments through the connection to the first universal adapter, and with a suction or aspiration apparatus through the connection to the second universal adapter.

A device can be configured such that a fluid can enter the device through the first universal adapter. The fluid can flow from the top housing to the bottom housing through the filters and exit the device through the second universal adapter. Accordingly, when the device is connected to a resecting and/or collecting tissue fragments device, and to a suction or aspiration apparatus; the resecting device can generate tissue fragments from a surgical site including a fluid. The tissue fragments can be contained within the fluid, which can flow through the filters, where the fragments can be collected in the filters based on their size. The top housing and the bottom housing can be partially of fully composed of translucent material so that the volume of tissue fragments collected in the filters can be visualized during the resection and collection process. Once an appropriate amount of material has been collected, the device can be disconnected from both the resecting and/or collecting device and from the suction or aspiration apparatus.

To access the collected material, the top housing and the bottom housing can be unscrewed or disconnected from one another, and the top housing removed. A portion of the filter distractor can extend out of the bottom housing. The distractor can be grasped, and the filters, assembled onto the filter distractor, together with the filter distractor, can be pulled out of the housing (e.g., either the top housing or the bottom housing). The filters can be configured so that they can be removed from the filter distractor individually, by sliding each filter out along the filter distractor. The material collected in the filter can then be easily accessed, removed from the filter, and processed as intended.

Assembly

An assembly can be configured to combine two or more variable particle size collection devices (e.g., 2, 3, 4, 5 or more) as described herein to provide for 2, 3, 4, 5, or more individual collection compartments. An assembly can be configured such that the two or more devices can be each connected through the first universal adaptor and the second universal adaptor, so that the devices can be assembled in parallel. In such configuration, a fluid can enter in the two or more devices simultaneously, or individually (e.g., into a first device and then into a second device). In this embodiment a hose or other suitable tubing connects the first universal adapter of each device to a device for resecting tissue fragments from a surgical site. In an embodiment the hose or other suitable tubing further comprises a valve. All hoses or other suitable tubing connected to each first universal adapter can be connected to the valve. The valve in turn can be connected via a hose or other suitable tubing to a device for resecting tissue fragments from a surgical site. In an embodiment, a hose or other suitable tubing connects the second universal adapter of each device to a suction or aspiration device. In an embodiment the hose or other suitable tubing connected to the second universal adapters further comprises a valve. All hoses or other suitable tubing connected to each second universal adapter can be connected to a valve. The valve in turn can be connected via a hose or other suitable tubing to an aspiration or suction device.

Figure 5:
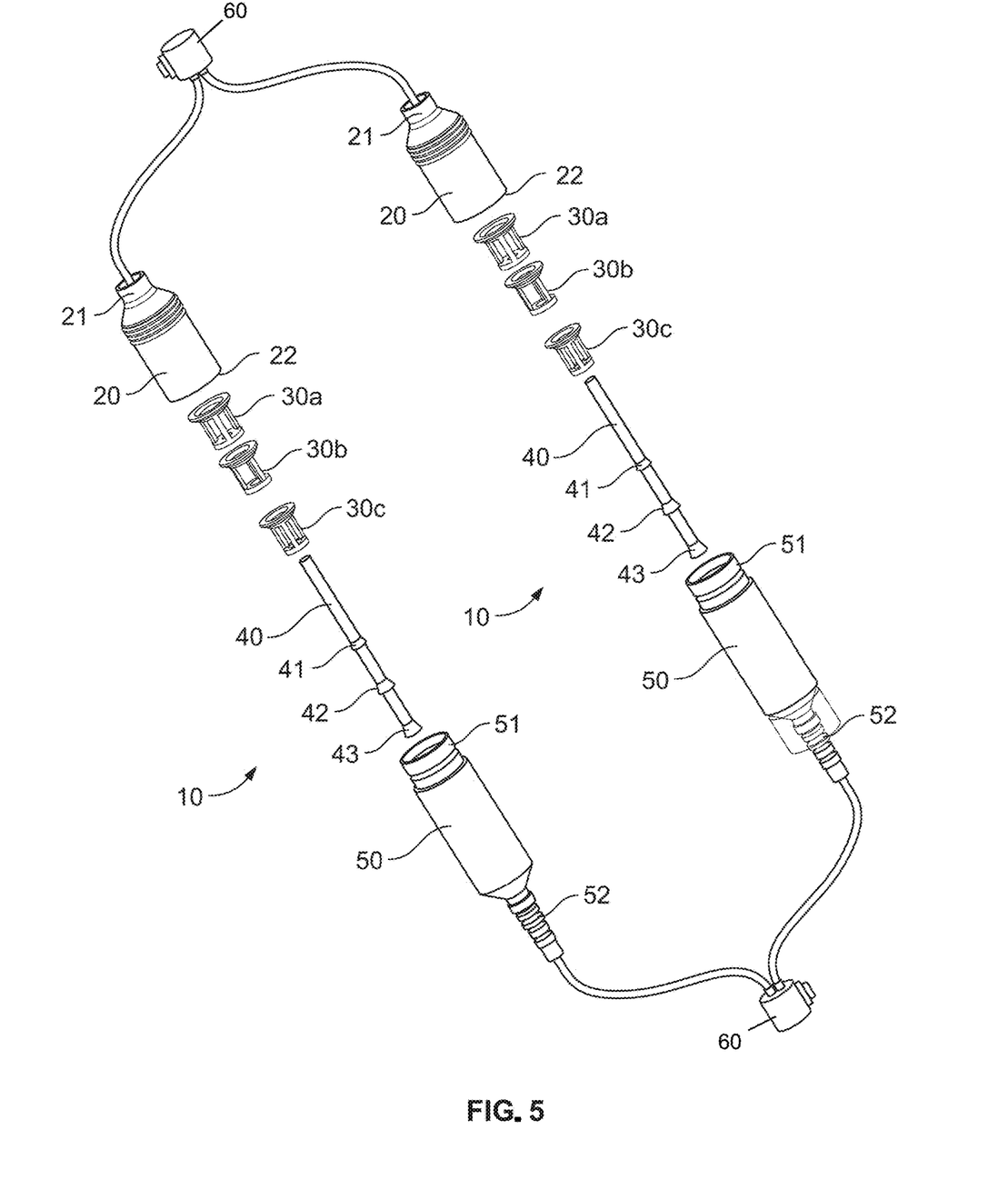
FIG. 5 illustrates an assembly for collecting tissue fragments of variable sizes from a surgical site comprising two or more devices.

Two or more devices can be assembled in parallel, as individual compartments, and a valve (60) can be connected so that fluid can be directed through the individual compartments at the same time or at different times. The valve (60) can be used to bypass the fluid away from one compartment.

A valve (60) can be used to direct fluid to and through the individual devices. Based on the quantity of material required, and for ease of collection, two or more devices can be assembled in parallel. In such a configuration the fluid comprising the tissue fragments can be diverted not only into one device but into the two or more devices, so that, e.g., larger amounts of material can be collected at once. The pore size of the filters in the two or more devices can be the same in all the devices, or can be different depending on the needs of the user. An adapter (e.g., any connective fitting) can be connected to a collection device or suction device, and to several tissue collector devices to ensure the distribution of the fluid from the collection device to several variable particle size collection devices, or from the several variable particle size collection devices to a suction device.

A valve (60) can be used to bypass fluid away from one device and to actively direct the fluid containing the particulate in a different device, or to divert said fluid from a desired device (i.e., for example when the filter collecting a particulate size of interest is full, and there is no need for the fluid to go through this device, the fluid can be diverted to allow the collection of more material of the size of interest in the additional devices). As used herein, the valve (60) can also be referred to as a switch. The valve (60) or switch can be used to control the delivery of the fluid to one or more of the devices or alternate delivery back and forth in the devices. For example, if during a tissue fragment collection process, different resecting devices are used, different size ranges of tissue fragment can be generated. A user can, using the valve (60), direct the fluid alternatively in several devices when using a first resecting device; and then, when using a second resecting device, reinstate a flow of fluid through devices that previously received fluid and tissue fragments.

Methods for collecting tissue fragments of separate, variable sizes using an assembly of two or more devices are provided. As described above, the devices can be provided fully assembled, and ready-to-use. A method can include the connection of each the two or more devices to an adaptor, the connection of the two or more devices with a second device for resecting tissue fragments, collecting tissue fragments, or resecting and collecting tissue fragments through the connection to the adaptor, and with a suction or aspiration apparatus through the connection to another adaptor.

To access the collected material, the individual devices can be separated from the assembly by disconnecting the devices from the first and the second universal adaptors; the top housing and the bottom housing can then be unscrewed or disconnected from one another, and the top housing removed. The material collected in the filters can then be easily accessed, removed from the filter, and processed as intended.

In another embodiment, 2 or more (e.g., 2, 3, 4, 5, or more) variable particle size collector devices can be connected in series. That is, a hose or other suitable tubing can be used to connect the second universal adapter of a first variable particle size collection device to the first universal adapter of a second device. The second universal adapter of the second variable particle size collection device can then be connected to an aspiration or suction device. The first universal adapter of the first device can be connected to a device for resecting tissue fragments from a surgical site.

Definitions

As used herein, a "fluid" is a liquid collected from surgical site into a subject. The subject can be a mammal, including but not limited to human, equine, canine, feline, bovine, porcine, rodent, sheep, or goat. The fluid comprise an isotonic solution, such as a saline solution or Ringer's lactate solution, which is commonly used to safely provide for surgical site irrigation during surgery. The fluid can include biological fluid, collected from the subject; it can be autogenic, allogenic, or xenogenic. Biological fluids include, but are not limited to, whole blood, plasma, serum, urine, saliva, mucus, cerebrospinal fluid, lymphatic fluid, seminal fluid, amniotic fluid, vitreous fluid, as well as fluid collected from cell culture of patient cells, and the like. Biological fluids also include fluids derived from tissue such as, for example, bone, bone marrow, muscle, brain, heart, liver, lung, stomach, small intestine, large intestine, colon, uterus ovary, testis, cartilage, soft tissue, skin, subcutaneous tissue, breast tissue, tissue obtained from other species, patient tissue from surgery, and the like. Biological fluids also can include, for example, bone marrow, fluids obtained from surgery, fluid filtrates, and the like.

As used herein, the term "tissue fragment" can refer to fragments, pieces, or debris obtained from a tissue during surgery. The tissue can be, e.g., soft tissue, bone or cartilage; and the tissue fragment can include bone or cartilage filtrates or fragments, bone/cartilage chips or fragments, or any other type of tissue pieces that can result from the treatment provided at the surgical site, obtained during surgery. The surgical site can be a joint, such as a knee, a shoulder, an ankle, an elbow, a hip, or a wrist. The tissue fragments can be collected for autologous graft.

The compositions and methods are more particularly described below and the Examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the embodiments claimed. Thus, it should be understood that although the present compositions and methods have been specifically disclosed by embodiments, optional features, modification and variation of the concepts herein disclosed can be resorted to by those skilled in the art, and that such modifications and variations are considered to be within the scope of these embodiments as defined by the description and the appended claims.

Any single term, single element, single phrase, group of terms, group of phrases, or group of elements described herein can each be specifically excluded from the claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the embodiments are described in terms of Markush groups or other grouping of alternatives, those skilled in the art will recognize that the embodiments are also thereby described in terms of any individual member or subgroup of members of the Markush group or other group.

What is claimed is:

1. A device for collecting tissue fragments of variable sizes from a surgical site comprising:
    a) a top housing comprising a first universal adapter,
    b) at least two filters each having a different pore size,
    c) a filter distractor comprising two or more ridges configured to hold the two filters in place on the filter distractor, and
    d) a bottom housing comprising a second universal adapter,
wherein the at least two filters are assembled in series through apertures in the bottom surfaces of the filters onto the filter distractor, wherein the at least two filters are removable from the filter distractor;
wherein the filter distractor and the at least two filters are inserted into the top housing or bottom housing; and
wherein the top housing and the bottom housing are assembled together into a container.

2. The device of claim 1, wherein the at least two filters each having a different pore size are assembled in series so that a fluid can flow from a filter having a larger pore size to a filter having a smaller pore size.

3. The device of claim 1, wherein each of the at least two filters is a cup-shaped filter having a bottom surface and one or more side walls.

4. The device of claim 3, wherein the bottom surface of the at least two filters comprises filter material, wherein the one or more side walls comprise filter material, or wherein the bottom of the at least two filters and the side walls comprise filter material.

5. The device of claim 3, wherein the filter distractor fits through the middle of the bottom surface of each cup-shaped filter, and wherein the filter distractor is optionally configured to remove tissue from the filters.

6. The device of claim 1, wherein the top housing comprises an internal screw thread and the bottom housing comprises an external screw thread, wherein the internal screw thread of the top housing is complementary to the external screw thread of the bottom housing.

7. The device of claim 1, wherein the top housing comprises an external screw thread and the bottom housing comprises an internal screw thread, wherein the external screw thread of the top housing is complementary to the internal screw thread of the bottom housing.

8. The device of claim 1, wherein the at least two filters are present as a modular assembly such that one or more filters can be removed or added to the filter distractor.

9. The device of claim 1, wherein the device is connected to a second device for resecting tissue fragments from a surgical site, wherein the second device is an endoscopic shaver, an endoscopic bone cutter, an endoscopic burr, or an endoscopic drill.

10. The device of claim 1, wherein the device is connected to a second device for collecting tissue fragments from a surgical site, wherein the second device is a suction wand.

11. A method of collecting tissue fragments of separate, variable sizes using the device of claim 1 comprising:
    a) connecting the first universal adapter of the device to a second device for resecting tissue fragments, collecting tissue fragments, or resecting and collecting tissue fragments;
    b) connecting the second universal adapter of the device to a suction or aspiration apparatus; and
    c) collecting tissue fragments on the at least two filters.

12. The method of claim 11, wherein the tissue is soft tissue, bone, or cartilage.

13. The method of claim 11, wherein the second device for resecting tissue fragments is an arthroscopic shaver, an arthroscopic bone cutter, an arthroscopic burr, or an arthroscopic drill.

14. The method of claim 11, wherein the device comprises three or more filters.

15. The method of claim 14, wherein a first filter has about 750 micron to about 850 micron pores; a second filter has about 350 micron to about 450 micron pores; and a third filter has about 50 micron to about 100 micron pores.

16. The method of claim 11, further comprising removing the top housing to access the filter distractor and the filters containing the tissue fragments of variable sizes; and pulling the filters out of the housing using the filter distractor.

17. An assembly for collecting tissue fragments of variable sizes from a surgical site comprising two or more devices, wherein each of the devices comprises:
    a) a top housing comprising a first universal adapter,
    b) at least two filters each having a different pore size,
    c) a filter distractor comprising two or more ridges configured to hold the two filters in place on the filter distractor, and
    d) a bottom housing comprising a second universal adapter,
wherein the at least two filters are assembled in series onto the filter distractor;
wherein the filter distractor and the at least two filters are inserted into the top housing or bottom housing; and wherein the top housing and the bottom housing are assembled together into a container;
wherein the two or more devices are each connected to a device for resecting tissue fragments from a surgical site though the first universal adapter and wherein the two or more devices are each connected to a suction or aspiration device through the second universal adaptor.

18. The assembly of claim 17, wherein the two or more devices are connected through the first universal adapter to a valve that can control the flow of fluid to the two or more devices.

19. A method of collecting tissue fragments of separate, variable sizes comprising:
    collecting tissue fragments on the at least two filters of the two or more devices of the assembly of claim 17.

20. The device of claim 3, wherein the cup-shaped filter is cylindrical shaped and wherein the bottom of the cup shaped filter is circular in shape.

21. The device of claim 3, wherein the cup-shaped filter is cylindrical shaped, and wherein the one or more side walls comprise filter material and the bottom surface comprises filter material.

22. The device of claim 20, wherein the cup-shaped filter has a solid top ring and a solid bottom ring.

23. The device of claim 3, wherein the cup-shaped filter comprises a solid top ring configured to rest on one or more ridges inside the bottom housing.

24. The device of claim 1, wherein an inside surface of the bottom housing comprises one or more ridges configured to provide support for the at least two filters.

25. The device of claim 17, wherein an inside surface of the bottom housing comprises one or more ridges configured to provide support for the at least two filters.

\* \* \* \* \*